United States Patent [19]

Annigeri et al.

[11] Patent Number: 5,539,656

[45] Date of Patent: Jul. 23, 1996

[54] CRACK MONITORING APPARATUS

[75] Inventors: Balkrishna S. Annigeri, Manchester; Leroy H. Favrow, Newington; Robert J. Haas, Coventry; Michael Winter, New Haven; Ronald I. Holland, Jr., East Hampton, all of Conn.; Jason S. Wegge, Springfield, Mass.; David M. Sanford, Colchester, Conn.

[73] Assignee: United Technologies Corporation, Hartford, Conn.

[21] Appl. No.: 321,349

[22] Filed: Oct. 11, 1994

[51] Int. Cl.$^6$ ........................................ G01B 9/08
[52] U.S. Cl. ..................... 364/507; 364/525; 364/579; 364/580; 73/788; 73/799; 73/800; 73/805; 356/23; 356/237; 382/141; 382/149
[58] Field of Search .......................... 364/361, 507, 364/508, 525, 563, 574, 579, 580; 73/577, 760, 788, 799, 800, 805, 806; 356/23, 32, 237; 382/16, 30, 34, 141, 149

[56] References Cited

U.S. PATENT DOCUMENTS

| | | | |
|---|---|---|---|
| 4,063,282 | 12/1977 | Exton | 358/106 |
| 4,175,447 | 11/1979 | Fukuhara | 73/799 |
| 4,233,849 | 11/1980 | Defebvre et al. | 73/812 |
| 4,364,113 | 12/1982 | Sengebusch et al. | 364/507 |
| 4,394,683 | 7/1983 | Liptay-Wagner et al. | 358/107 |
| 4,572,663 | 2/1986 | Greene et al. | 356/23 |
| 4,574,642 | 3/1986 | Fleischman | 73/799 |
| 4,653,109 | 3/1987 | Lemelson et al. | 382/34 |
| 4,875,170 | 10/1989 | Sakurai et al. | 364/507 |
| 5,047,851 | 9/1991 | Sauerwein et al. | 358/101 |

OTHER PUBLICATIONS

System Description and Operating Instructions for Model PN–232 entitled "Laser–Augmented Welding Vision System" manufactured by Control Vision, Inc.

Documentation entitled "Some Benefits of Laser–Enhanced Welding Vision" by Control Vision, Inc.

Documentation entitled "Laser Video for Welding . . . Arc Welding Without the Arc!" by Control Vision, Inc.

Paper entitled "Measurement of Small Cracks by Photomicroscopy: Experiments and Analysis" by James M. Larsen et al.

ASTM Special Technical Publication 1149, pp. 92–115, W. N. Sharpe, Jr. et al., "Real–Time Measurement of Small–Crack Opening Behavior Using an Interferometric Strain/Displacement Gage".

Primary Examiner—Emanuel T. Voeltz
Assistant Examiner—Craig S. Miller
Attorney, Agent, or Firm—Pamela J. Curbelo

[57] ABSTRACT

An apparatus for monitoring the growth of surface cracks in materials includes a means for applying a load to a specimen to simulate actual use of the specimen, means for illuminating the specimen, means for capturing images of the specimen, and means for processing the images to monitor crack growth in the specimen. Optionally, the means for processing can be used to control the other means.

20 Claims, 3 Drawing Sheets

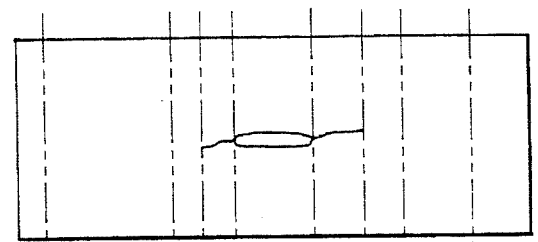
*fig.3A* $t_0$
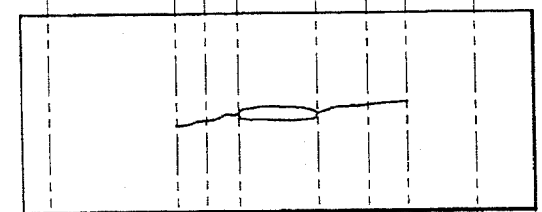
*fig.3B* $t_1$
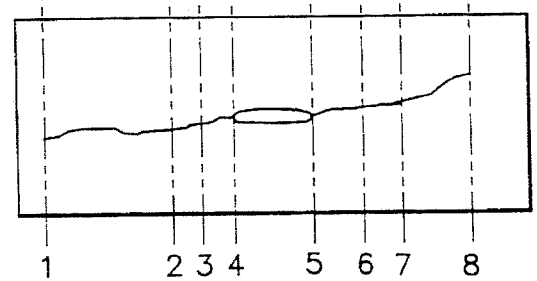
*fig.3C* $t_2$
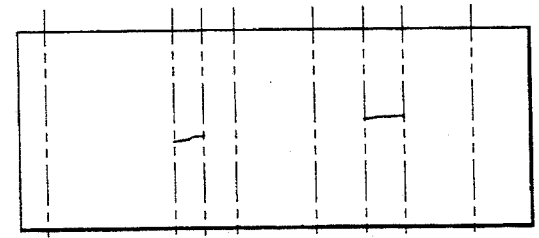
*fig.4A* $t_1 - t_0$
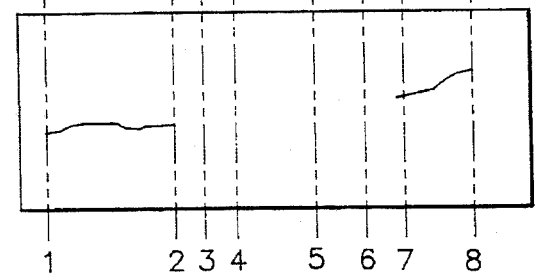
*fig.4B* $t_2 - t_1$ $t_1 - t_0$ $t_2 - t_1$ $t_1 - t_0$ $t_2 - t_1$

CRACK MONITORING APPARATUS

TECHNICAL FIELD

This invention relates to an apparatus for monitoring crack growth in materials while under a load.

BACKGROUND INFORMATION

In material and product development, there is a need to understand material behavior before integration thereof into a final product. Therefore, there has been a need to characterize the mechanical properties of materials. For example, materials under a prolonged cyclic loading can undergo catastrophic failure due to initiation of cracks and their rapid growth. Consequently, emphasis has been placed on understanding the behavior of materials during cyclic loading; and especially during cyclic loading which simulates how that material will actually be used.

Most conventional apparatus, however, cannot measure crack formation and propagation during cyclic loading of a material. Therefore, testing of a material using a typical cyclic loading regime creates many problems. For example, monitoring surface crack formation and propagation comprises capturing an image, usually by still photography, and measuring the crack's dimensions from that image. Because the movement of the specimen during cyclic loading does not allow for clear photographic images, the loading regime must be stopped, periodically, for photographic work. Stopping the loading regime is time consuming and it allows the material to relax which is outside of the intended loading regime. Consequently, this conventional technique can lead to anomalous results.

Another method of monitoring crack growth, which has problems similar to the still photography, comprises surface replication coupled with the use of a Transmission Electron Microscope (TEM). Here the loading regime is periodically stopped to make an acetate replicate of a surface of the specimen. The replicate is then viewed under a TEM to observe crack formation and growth. This method not only comprises an undesirable relaxation period, it is very time consuming and expensive.

In addition to long down times, high cost, and alterations of the anticipated loading regime, the analysis of crack growth typically proceeds by manual calculations requiring physical measurements of the photos. The measurements are performed by placing a reference mark of predetermined length on the specimen prior to testing such that the crack lengths can be measured with respect to the reference mark. The changes in crack size can be calculated directly from the measurements of the crack, or the total crack size is determined by comparing the length of the crack to the reference mark. Since this technique includes several points of human intervention, there is a potential for error. This limitation of the monitoring apparatus can lead to an increased error in the characterization of a material, high cost, and long test periods.

Another drawback of conventional apparatus is a lack of automatic shut off based upon crack size. Because a specimen can undergo thousands of load cycles during a test, the point of crack initiation is often not recorded and the specimen is cycled until failure. Consequently, some of the early stage characteristics of a surface crack are destroyed, rendering that test specimen less valuable since the shape and pattern of a crack initiation and growth are needed for subsequent crack growth modeling.

Therefore, what is needed in the industry is an apparatus capable of accurately measuring crack growth on a specimen during the application of a load, determining a crack's dimensions in real time, and terminating the loading when the crack reaches a predetermined dimension.

SUMMARY OF THE INVENTION

The present invention relates to a method and apparatus for monitoring cracks in a specimen. The apparatus of the present invention comprises a means for applying a load to the specimen, means for illuminating the specimen, means for capturing an image of the specimen, and means for processing the captured image to monitor crack growth in the specimen.

The method of the present invention comprises applying a load to the specimen, illuminating the specimen during the application of the load to accentuate the formation of cracks, capturing images of the specimen during the loading regime, wherein said illuminating and capturing are synchronized with one another, and processing the captured images.

BRIEF DESCRIPTION OF THE DRAWINGS

FIGS. 3A–3C show images of cracks at different points in time in the loading regime.

FIGS. 4A–4B show the changes in a crack's dimensions after subtracting out a previous image.

BEST MODE FOR CARRYING OUT THE INVENTION

Figure 1:
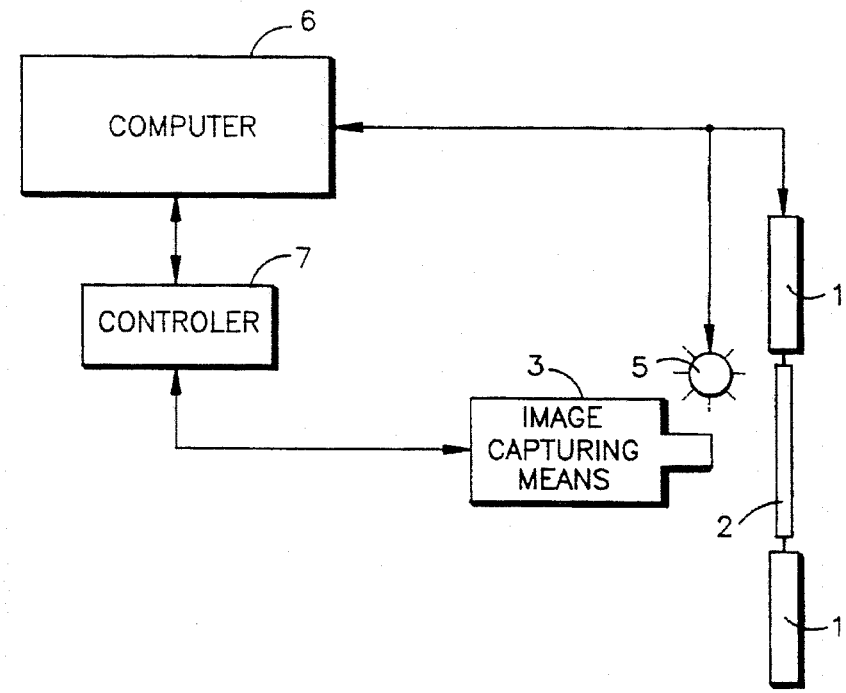
FIG. 1 is an overall schematic of the invention.

An embodiment of the apparatus of the present invention as illustrated in FIG. 1 includes: means for applying a load 1 to a specimen 2 to simulate actual use, means for illuminating 5 the specimen 2 to accentuate the formation of cracks on the specimen, means for capturing images 3 of the specimen 2, means for processing the images 6 to monitor changes in a crack's dimensions during the loading regime. Optionally, a means for controlling 7 the loading means 1, illuminating means 5, and the image capture means 3 can be attached to the processing means 6 to implement the results obtained from the processing means 6 to control the operation of the other means. For example, the load or cycle rate can be increased or decreased, the loading can be terminated when the crack reaches a predetermined length, and the illumination means 5 and capture means 3 can be positioned to obtain better light contrast.

The means for applying a load 1 can be any conventional device that can impart a loading regime to a specimen, with a means which can closely simulate the loading regime of an actual component formed from the material of the specimen, generally preferred. These devices include servo-hydraulic and electric test machines, such as a 3310 series, 100 kN capacity, universal testing machine produced by Interlaken Technology Corporation (Minnesota, USA). Similar machines are produced by Instron Corporation, Canton, Mass. and MTS Systems Corporation, Minneapolis, Minn., among others.

While the loading means 1 applies a load to the specimen 2, the illuminating means 5 illuminates the specimen 2 to allow monitoring of crack formation and growth. Since monitoring typically occurs at a microscopic level, surface preparation of the specimen can be very important in order to obtain the desired illumination and contrast of any cracks which form. Typically, conventional surface preparation techniques can be used either alone or combinations thereof, such as the ASTM preparation standards. The specimen should be prepared to obtain preferential etching of the specimen such that grain boundaries and other microstructural features will not be highlighted to the point that these boundaries and features can not be distinguished from cracks.

The illuminating means 5 may be any conventional lighting device that casts a light sufficient to illuminate at least a surface of the specimen 2 and preferably provides considerable flexibility in illuminating the area of the specimen where cracks occur. Generally, any conventional strobe light capable of strobing at least at the frequency of the loading means 1 and preferably at the frequency of the image capturing means 3, can be employed. Fiber optic light guides capable of directing the light from a short duration strobe are particularly useful due to their small size, flexibility, and efficiency in transferring the light from the strobe source to the surface under study. One such fiber optic light is produced by Dolan Jenner, Woburn, Mass., USA.

The orientation of the illuminating means 5 is important due to the desire to obtain maximum image contrast for observing the crack and thereby enhance the accuracy of the crack monitoring. Typically the illuminating means 5's location, with respect to the surface of the specimen 2, is dictated either by the presence of a surface notch which sets up a crack formation site or by the geometry of the specimen. Note, surface feature contrast is particularly important when monitoring shallow cracks which do not usually provide sufficient contrast in lighting and shadowing to enable accurate crack monitoring.

Additionally, in order to allow proper comparison of images and therefore proper crack growth monitoring, it is preferred that the illuminating means 5 illuminate the specimen 2 for as short a time as possible. Short illumination times enable the capture of images only at a predetermined point or phase in the loading regime, thereby reducing or eliminating image blur due to subject motion and enhancing image accuracy. Times on the order of a few nanoseconds up to about 10 microseconds ($\mu$sec) can be used, with less than about 5 $\mu$sec preferred, and less than about 1.5 $\mu$sec especially preferred. The illuminating time may be determined by the specimen's velocity which is a function of the magnitude and variation of the load and composition of the specimen 2, with consideration given to the magnification used by the imaging means 3.

To further ensure image capture at a desired point in the loading regime, the loading means 1 and the illumination means 5 can be synchronized, i.e. operated in phase ("phased"), so that illumination only occurs at the desired points in the loading regime. For example, the loading means 1 and illumination means 5 can be synchronized so that illumination and image capture both occur when the load is at the point of maximum crack opening.

Also synchronized with the loading means 1 and the illuminating means 5, is at least one means for capturing images 3. This image capturing means 3 can be any conventional imaging device capable of sufficiently capturing the image of a crack such that its growth can be monitored and preferably visually recorded. For example, conventional National Television Standard Commission, "NTSC", video systems can be used with the present invention in conjunction with a conventional magnification device such as a conventional microscope, macrophoto lens, or electronic image magnification device. The magnification device is typically used to clarify the video image.

The desired resolution capabilities of the image capturing means, which can readily be determined by an artisan, are typically about 0.5 mils (12.7 microns ($\mu$)) or less, with about 0.1 mil (2.54 $\mu$) preferred. In one application, for example, two Panasonic WV CD-20 video cameras having about 200× system magnification and 12.7 $\mu$resolution capability were used to monitor two sides of a specimen where crack formation was estimated to occur based on the geometry of the specimen. The cameras can be mounted on a device, such as a tripod or other support device, i.e. x, y, z stage, which enables focusing on any desired point on the specimen.

Also employed to allow real time monitoring of crack formation and growth is a processing means 6 which connects to and utilizes the image from the image capturing means 5. This processing means 6 can be any conventional device capable of real time processing of the data from the image capturing means, such as a device capable of digital processing the data from the image capture means 5 to automatically extract crack growth data. One such device is a two dimensional imaging computer system capable of quantitatively analyzing recorded crack growth data using software that real time image processes that data. This software, which can be any software capable of processing the crack growth data, preferably provides real time zoom and enhancement capabilities and effectuates two dimensional imaging. For example, OMA software developed by M. Long at Yale University (New Haven, Conn., USA) can be used for quantitative analysis and image processing and IMAGE software developed by the National Institutes of Health (Bethesda, Md., USA) can be used for real time monitoring of the image capturing means' signals and for providing real time zoom and enhancement capability for crack detection.

Figure 2:
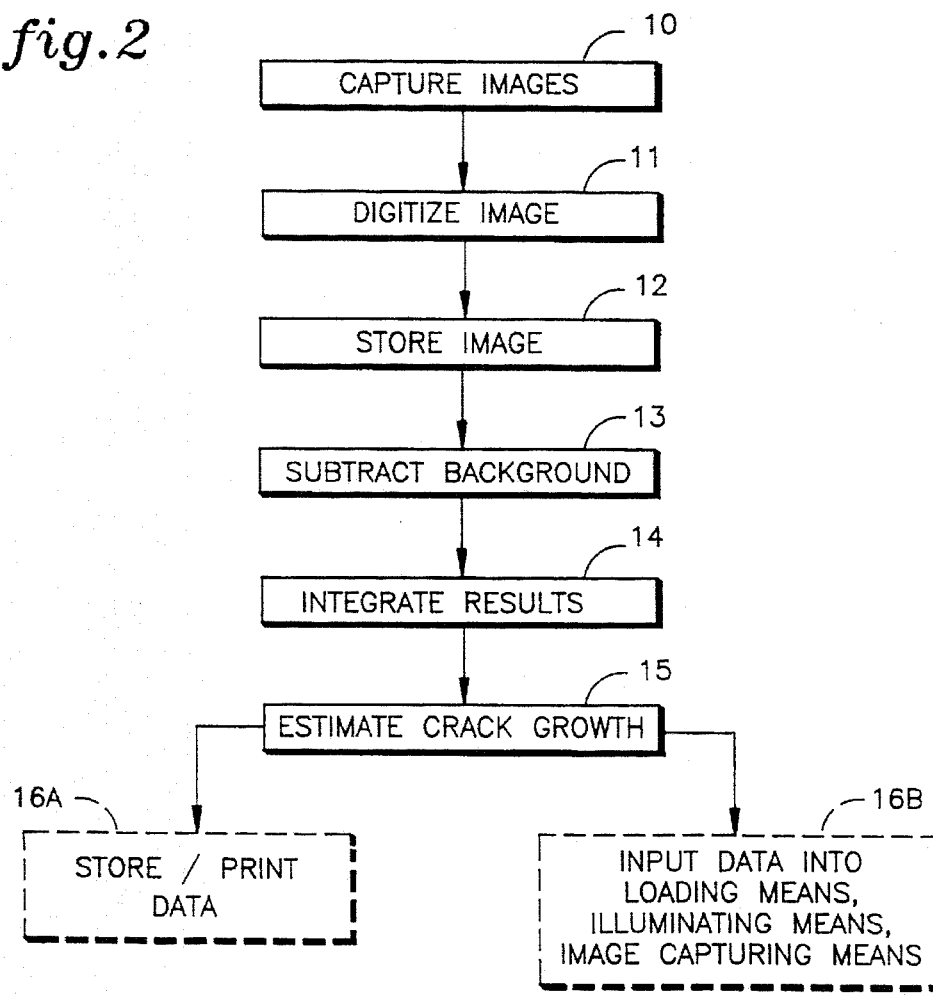
FIG. 2 is a block diagram of the processing means used to monitor the changes in a crack's dimension.
Figure 5A:
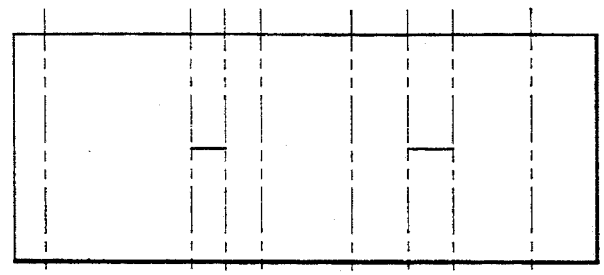
FIGS. 5A–5B show the integration of the changes in the crack into a single vector axis.
Figure 5B:
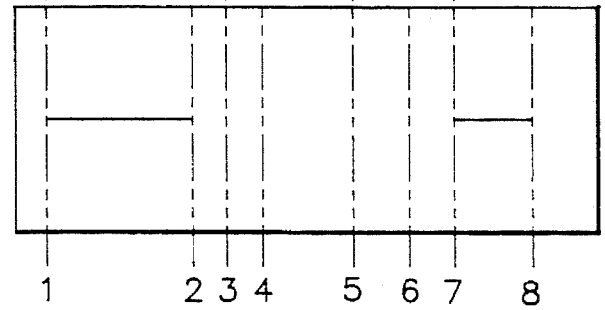

FIG. 2 illustrates the flow of data through the processing means 6. This set up enables digitization of the images allowing the computer to subtract out background images (see below) and concentrate on changes in a crack's dimensions. An image is captured 10, computer digitized 11, and stored 12. The computer then subtracts a previously captured and digitized image (the background) 13 from the new image, records the difference between the two images, and integrates across the crack 14 to show the change in the crack's size and location along a single vector axis. This data can then be analyzed accordingly. For example, mean crack growth 15 can be determined by comparing the center point of the location and size of the 5 crack along a single vector axis, the "centroid", of the portion of the crack that is left after the background has been subtracted away, the "crack tips".

Figure 6A:
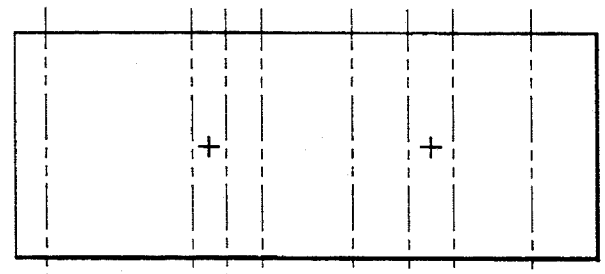
FIGS. 6A–6B show the location of the centroid of the crack tips.
Figure 6B:
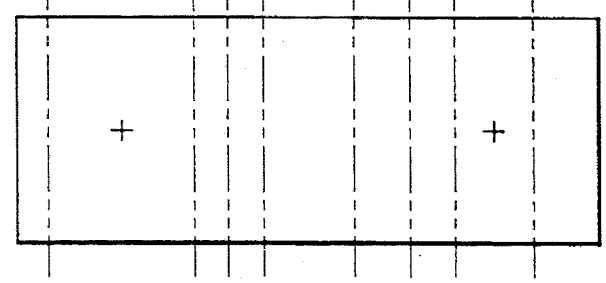

FIGS. 3A–6B illustrate the operations of the processing means 6. FIGS. 3A–3C show a crack image at three different times during a loading regime. FIGS. 4A–4B illustrate the subtraction of an image from the background. In FIGS. 5A–5B, the subtracted images are integrated to be represented on one axis. In FIGS. 6A–6B, the centroid of the crack (represented at this point as a single direction vector) is located so the computer can estimate the crack growth. The mean crack growth data can then be printed and/or stored 16A (see FIG. 2), recording the entire crack formation, or if desired, only the changes in the specimen's surface topography.

EXAMPLE

The following example was used to monitor crack growth in a 0.03 inch (0.762 mm) aluminum specimen.

1. An aluminum specimen was prepared using conventional electropolishing techniques by placing the specimen in 220 milliliters (ml) water, 200 ml glycerol, and 580 ml sulfuric acid for about 45 minutes with a voltage of about 6 volts.
2. The specimen was then placed in a servo-hydraulic test machine which applied a stress level of 11.25 ksi, at a loading frequency of 30 Hz, for about 18,000 cycles.
3. While the load was applied to the specimen, the specimen was illuminated with a strobe having a frequency of 30 Hz and video with a video camera having a frequency of 30 Hz, using a macrophoto lens to obtain a system magnification of 200×.
4. The data collected by the video camera was processed by a computer using OMA software for quantitative analysis and IMAGE software for real time monitoring.

Since automated synchronization of the loading means 1, the illuminating means 5, and image capturing means 3 will improve the capture of images at a predetermined point in the loading regime, a controlling means can optimally be attached to the processing means 6 to control the other means (see 16B of FIG. 2). The controlling means 7 can use data obtained from the processing means 6 to alter the load during deformation at the site of a crack or to stop the loading when a crack reaches a predetermined size, and to locate a site of crack formation on a specimen surface and move the image capturing means 3 and illuminating means 5 to focus upon that site. Ultimately, the controlling means 7 can be used to automatically operate the entire or any part of the apparatus by using data from an operator and/or output from the processing means 6.

Although the invention has been described and illustrated with respect to the exemplary embodiments thereof, it should be understood by those skilled in the art that the foregoing and various other changes, omissions and additions may be made without departing from the spirit and scope of the invention.

We claim:

1. An apparatus for monitoring cracks in a specimen, comprising:
   a. means for applying a load to a specimen, wherein said means for applying a load has a frequency;
   b. means for illuminating the specimen during the application of a load, wherein said illuminating means has a frequency greater than or equal to said frequency of said means for applying a load;
   c. means for capturing images of the specimen, wherein said capturing means is synchronized with said illuminating means such that crack formation images can be obtained during the application of a load;
   d. means for processing images obtained by said image capturing means to produce crack data real-time; and
   e. a means for controlling having a means for receiving data from said processing means or data input by an operator wherein said means for controlling controls said means for applying a load, said illuminating means, or said image capturing means by using data from said processing means or said data input by an operator.

2. The apparatus of claim 1, wherein said means for applying a load is for applying a loading regime to the specimen which simulates of the loading regime of an actual structural component composed of the same material as the specimen.

3. The apparatus of claim 1, wherein the means for illuminating the specimen and the specimen are arranged to provide as much image contrast as possible.

4. The apparatus of claim 1, wherein said frequency of said illuminating means and said means for applying a load are synchronized.

5. The apparatus of claim 1, wherein the means for processing includes means for digitizing a first captured image, storing said first captured-digitized image, digitizing a second captured image, then subtracting out the first captured-digitized image from said second captured-digitized image, integrating the subtracted images, and estimating crack growth.

6. The apparatus of claim 1, further comprising a means for storing and printing the crack growth data.

7. The apparatus of claim 1 wherein said means for illuminating comprises fiber optic light guides.

8. The apparatus of claim 1, wherein said image capturing means includes a magnification means.

9. The apparatus of claim 8, wherein said magnification means is a microscope, a macrophoto lens, or an electronic magnification means.

10. A method for monitoring cracks in a specimen, comprising the steps of;
    a. applying a load to the specimen with a means for applying a load, wherein said means for applying a load has a frequency;
    b. illuminating the specimen during the application of the load to accentuate the formation of cracks with an illuminating means having a frequency greater than or equal to the frequency of the means for applying a load;
    c. capturing images of the specimen during the loading regime, wherein said illuminating and capturing are synchronized with one another;
    d. processing the captured images to obtain crack data real-time; and
    e. controlling, with a means for controlling having a means for receiving data from said processing means or data input by an operator, said means for applying a load, said illuminating means, or said image capturing means by using data from said processing means or said data input by an operator.

11. The method of claim 10, wherein the loading regime is applied to the specimen to simulate the loading regime of an actual structural component composed of the same material as the specimen.

12. The method of claim 10, wherein the specimen is oriented to provide as much image contrast as possible during illumination.

13. The method of claim 10, wherein said illumination and said application of a load occur at synchronized frequencies.

14. The method of claim 10, wherein said illumination and said image capturing occurs at a like point in the loading regime.

15. The method of claim 10, wherein said illumination and said image capturing occur at a point in the loading regime where a crack is opened to its maximum dimension.

16. The method of claim 10, wherein said processing includes digitizing a first captured image, storing said first captured-digitized image, subtracting out the first captured image from a second captured-digitized image, integrating the subtracted images, and estimating crack growth.

17. The method of claim 10, further comprising storing and printing the crack growth data.

18. The method of claim 10, wherein the specimen is illuminated with fiber optic light guides.

19. The method of claim 10, further comprising magnifying the image.

20. The method of claim 10, further comprising preparing the specimen such that grain boundaries and other microstructural features will not inhibit the monitoring of cracks.

* * * * *